(12) United States Patent
Chung

(10) Patent No.: US 9,908,795 B2
(45) Date of Patent: Mar. 6, 2018

(54) APPARATUS FOR GENERATING FUNCTIONAL WATER

(71) Applicant: KOREA BIO TECHNOLGY ENT., Gwangju (KR)

(72) Inventor: Yong Kyun Chung, Seoul (KR)

(73) Assignee: KOREA BIO TECHNOLOGY ENT., Gwangju (KR)

( * ) Notice: Subject to any disclaimer, the term of this patent is extended or adjusted under 35 U.S.C. 154(b) by 1 day.

(21) Appl. No.: 14/782,310

(22) PCT Filed: Jan. 30, 2015

(86) PCT No.: PCT/KR2015/001011
§ 371 (c)(1),
(2) Date: Oct. 2, 2015

(87) PCT Pub. No.: WO2015/167112
PCT Pub. Date: Nov. 5, 2015

(65) Prior Publication Data
US 2017/0036927 A1    Feb. 9, 2017

(30) Foreign Application Priority Data
May 1, 2014    (KR) .................. 10-2014-0053090

(51) Int. Cl.
*B65D 1/02*    (2006.01)
*B65D 41/04*    (2006.01)
(Continued)

(52) U.S. Cl.
CPC .......... *C02F 1/4676* (2013.01); *B65D 1/0246* (2013.01); *B65D 41/04* (2013.01);
(Continued)

(58) Field of Classification Search
CPC ...... B01F 1/0027; B01F 1/0033; B01F 3/125; B65D 1/0246; B65D 41/04; B65D 51/24; B65D 51/28; C02F 1/4676; C02F 1/66; C02F 1/68; C02F 1/685; C02F 1/687; C02F 1/688; C02F 2201/46165; C02F 2307/02
See application file for complete search history.

(56) References Cited

U.S. PATENT DOCUMENTS 3,079,022 A * 2/1963 Tompkins ............. B65D 51/28
                                                          215/227
5,013,459 A * 5/1991 Gettings ................ C02F 1/688
                                                          210/282
(Continued)

FOREIGN PATENT DOCUMENTS

JP    2010-075804 A    4/2010
KR    20-0282596 Y1    7/2002
(Continued)

*Primary Examiner* — Lucas Stelling

(57) ABSTRACT

Disclosed is an apparatus for generating functional water which allows a container to be connected to a water bottle with an opening part which is standardized and available in the market, thus reducing water filled in the water bottle into functional water which is formed of oxygen water, sterilized and deodorized water, hydrogen or ionized water. The apparatus includes a container which accommodates a functional water generating member, wherein the upper and lower sides are blocked by an upper plate and a lower plate; and a water bottle connection part which is formed in the center of the upper plate while communicating with the inside of the container and is configured to connect separable the opening part of the water bottle.

6 Claims, 7 Drawing Sheets

(51) Int. Cl.
    *B65D 51/28*     (2006.01)
    *C02F 1/00*     (2006.01)
    *C02F 1/467*     (2006.01)
    *C02F 1/66*     (2006.01)
    *C02F 1/68*     (2006.01)

(52) U.S. Cl.
    CPC .............. *B65D 51/28* (2013.01); *C02F 1/003* (2013.01); *C02F 1/66* (2013.01); *C02F 1/688* (2013.01); *C02F 2201/46165* (2013.01); *C02F 2307/02* (2013.01)

(56) References Cited

U.S. PATENT DOCUMENTS

| | | | | |
|---|---|---|---|---|
| 5,681,463 | A * | 10/1997 | Shimizu | C02F 1/003 210/266 |
| 6,527,110 | B2 * | 3/2003 | Moscovitz | B65D 51/2835 206/222 |
| 2005/0051476 | A1 * | 3/2005 | Chen | C02F 1/003 210/436 |
| 2005/0184024 | A1 * | 8/2005 | Santa Cruz | B65D 51/28 215/227 |
| 2010/0012193 | A1 * | 1/2010 | Anson | C02F 1/002 137/1 |
| 2012/0017766 | A1 * | 1/2012 | Anson | B65D 51/28 99/290 |

FOREIGN PATENT DOCUMENTS

| | | |
|---|---|---|
| KR | 10-2012-0016958 A | 2/2012 |
| KR | 10-2013-0049909 A | 5/2013 |

\* cited by examiner

APPARATUS FOR GENERATING FUNCTIONAL WATER

TECHNICAL FIELD

The present invention relates to an apparatus for generating functional water, and in particular to an apparatus for generating functional water wherein water in a water bottle can be converted into functional water which is formed of oxygen water, sterilized and deodorized water or ionized water (reduced water) in such a way to directly connect a water bottle the opening part of which is standardized in size, and the whole volume can be minimized, and any water bottle with a threaded opening part or an opening part having circumference protrusions can be compatibly connected.

BACKGROUND ART

In general, drinking water, for example, mineral water, etc. is stored in a transparent container with a sealing cap. Such a sealing type transparent container is available in various types, for example, a bottle shape, etc. depending on contents which are filled.

In recent years, health is becoming a big issue, so a new type of a container is used in order to generate and store natural health foods. To this end, alkali reduced water is receiving attention so as to remove oxygen free radical or acidic wastes which are regarded as an aging or adult disease factor in a human body. Various methods and apparatuses are being developed in an effort to generate alkali reduced water.

As an example of a conventional container for generating alkali reduced water, there is the Korean patent registration number 1301904 entitled "container for accommodating liquid" (hereinafter referred to as "conventional container for accommodating liquid") which was invented and patented by the same applicant as the present invention. The above conventional container will be described below.

The above conventional container for accommodating liquid includes a container formed of an upper layer part having a hollow empty space and open upper and lower sides, and a lower layer part which is formed extending downward from the upper layer part and has an empty space in its inside, thus accommodating liquid; and an upper and lower side separating plate which fits movable into a boundary part formed between the upper layer part and the lower layer part of the container, thus forming an air block layer at the lower layer part, wherein the upper and lower side separating plate includes a plurality of through ventilation holes, and each of the ventilation holes is formed in a conical shape wherein the diameter of the upper side is smaller than the diameter of the lower side, more specifically, in a conical shape wherein the upper side is narrow, and lower side is wide.

An alkali reducing agent is provided at the lower layer part, thus reducing the liquid filled in the inside of the container into alkali reduced water.

In the above-described conventional container for accommodating liquid, the upper layer part into which water is filled and the lower layer part into which an alkali reducing agent is filed are formed in a single container. For this reason, the conventional container for accommodating liquid becomes bulky in terms of its whole volume since the upper layer part into which water is filled and the lower layer part are configured integral.

Therefore, the conventional container for accommodating liquid causes inconvenience since the whole volume is large when a user carries it in person for an outdoor activity, for example, exercise or travel.

DISCLOSURE OF INVENTION

Accordingly, the present invention is made in an effort to resolve the above-mentioned problems. It is an object of the present invention to provide an apparatus for generating functional water wherein water in a water bottle can be converted into functional water which is formed of oxygen water, sterilized and deodorized water or ionized water (reduced water) in such a way to directly connect a water bottle the opening part of which is standardized in size, and the whole volume can be minimized.

It is anther object of the present invention to provide an apparatus for generating functional water which allows a container to be compatibly connected to a water bottle wherein the outer diameter of an opening part with a threaded part is small or a water bottle wherein the outer diameter of an opening art with a threaded part is large or a water bottle which includes circumference protrusions.

It is further another object of the present invention to provide an apparatus for generating functional water which is able to prevent grain-shaped alkali reducing agent from inputting into a water bottle in such a way to provide a water passage plate at a lower side of a first connection pipe.

It is still further another object of the present invention to provide an apparatus for generating functional water which is able to prevent a water bottle from standing inclined in a state wherein the water bottle is placed upside down in such a way to form a circumference protrusion plate wherein an upper circumference of the water bottle contacts close with the circumference of an upper plate of a container. In addition, it is possible to prevent the inputs of any impurities, for example, dust, etc. into the inside of the container in such a way to provide a separable opening and closing cover at the top of the container.

It is still further another object of the present invention to provide an apparatus for generating functional water which allows to prevent the loss of a separable opening and closing cover in such a way to form a lower engaging screw part which is provided to store the separable opening and closing cover at a lower side of a circumferential surface of a container.

It is still further another object of the present invention to provide an apparatus for generating functional water wherein a functional water generating part with an electrode can be easily operated indoor or outdoor in such a way to operate, using a charging part, a functional water generating part having an electrode.

To achieve the above object, there is provided an apparatus for generating functional water, which may include, but is not limited to, a container which is configured to accommodate a functional water generating unit, wherein its upper and lower sides are blocked by an upper plate and a lower plate; and a water bottle connection part which is formed in the center of the upper plate while communicating with the inside of the container, wherein the water bottle connection part connects separable an opening part of the water bottle.

In addition, according to the apparatus for generating functional water of the present invention, the water bottle connection part may include, but is not limited to, a first connection pipe which stands vertical protruding downward in the center of the upper plate and is formed of a first tap part formed at a circumference in the inside thereof, wherein a threaded part formed on an outer circumferential surface of the opening part of the water bottle is engaged to the first tap part.

In addition, according to the apparatus for generating functional water of the present invention, the water bottle connection part further may include, but is not limited to, a second connection pipe which is engaged separable to the first tap part, wherein a threaded part formed on an outer circumferential surface of the opening part of the water bottle is engaged to the second connection pipe, wherein the second connection pipe includes a size contracted pipe part which is formed at a lower portion thereof and has a connection screw part formed at an outer circumferential surface thereof and engaged to the first tap part; and a size enlarged pipe part which integrally extends from the top of the size contracted pipe part with the inner diameter enlarging, wherein on an inner circumferential surface thereof, a second tap part is formed, the pitch circle of which expands larger than the pitch circle of the first tap part.

In addition, according to the apparatus for generating functional water of the present invention, the water bottle connection part may include a rubber connection packing pipe which is formed in a cylindrical shape and fits into the inside of the second tap part of the second connection pipe, wherein a chamfering part is formed at a circumference of the top of the inside, and a circumference protrusion formed on an outer circumferential surface of the opening of the water bottle is inserted in an interference fit way.

In addition, according to the apparatus for generating functional water of the present invention, the functional water generating unit is formed of an alkali reducing agent provided in a grain type or a single solid form, and a water passage plate with a plurality of water passage holes is further fixed at a lower side of the first connection pipe.

In addition, according to the apparatus for generating functional water of the present invention, the container may include, but is not limited to, a separable opening and closing cover configured to cover the top of the container, wherein there are provided a circumference protruding plate which is formed protruding upward from an upper side of a circumference of the upper plate; an upper engaging screw part formed on an outer circumferential surface of the circumference protruding plate; and an engaging tap part which is formed on an inner circumferential surface of the circumference plate and is engaged separable to the upper engaging screw part.

In addition, according to the apparatus for generating functional water of the present invention, the container may include a lower engaging screw part which is formed on a lower side of an outer circumferential surface of the container, wherein an engaging tap part formed on a circumference plate of the separable opening and closing cover is engaged to the lower engaging screw part.

In addition, according to the apparatus for generating functional water of the present invention, the functional water generating unit may include, but is not limited to a charging part having a charging battery fixed at the top of the lower plate of the container; an electric power supply jack which is connected to the charging part and extends to a circumference of the container; a substrate which is fixedly arranged on the top of the charging part and is connected with the charging unit; a switch which is connected to the substrate and extends toward a circumference of the container; and an electrode which is fixedly arranged horizontal on the top of the substrate and performs electrolysis with respect to water.

Advantageous Effects

According to the present invention, water in a water bottle can be converted into functional water which is formed of oxygen water, sterilized and deodorized water or ionized water (reduced water) in such a way to directly connect a water bottle the opening part of which is standardized in size, and the whole volume can be minimized since it does not need to form a space to fill with water, thus providing convenience in carrying when a user does an outdoor activity, for example, exercise or travel.

In addition, the apparatus for generating functional water allows a container to be compatibly connected to a water bottle wherein the outer diameter of an opening part with a threaded part is small or a water bottle wherein the outer diameter of an opening art with a threaded part is large or a water bottle which includes circumference protrusions. Since the apparatus is made of a synthetic resin material or a glass material, it can allow a container to be connected to almost all kinds of water bottles which are standardized and available in the market.

Since the apparatus for generating functional water is able to prevent grain-shaped alkali reducing agent from inputting into a water bottle in such a way to provide a water passage plate at a lower side of a first connection pipe, thus obtaining stability when in use while preventing any loss of the alkali reducing agent.

In addition, the apparatus for generating functional water is able to prevent a water bottle from standing inclined in a state wherein the water bottle is placed upside down in such a way to form a circumference protrusion plate wherein an upper circumference of the water bottle contacts close with the circumference of an upper plate of a container, thus obtaining stability during a procedure wherein water is converted into functional water by moving the water bottle. In addition, it is possible to prevent the inputs of any impurities, for example, dust, etc. into the inside of the container in such a way to provide a separable opening and closing cover at the top of the container, thus obtaining more sanitary operations.

The apparatus for generating functional water allows to prevent the loss of a separable opening and closing cover in such a way to form a lower engaging screw part which is provided to store the separable opening and closing cover at a lower side of a circumferential surface of a container.

In addition, in the apparatus for generating functional water, a functional water generating part with an electrode can be easily operated indoor or outdoor in such a way to operate, using a charging part, a functional water generating part having an electrode, thus providing convenience when in use.

BRIEF DESCRIPTION OF DRAWINGS

FIG. 4 is a view illustrating a use state of an apparatus for generating functional water according to the present invention.

Figure 1:
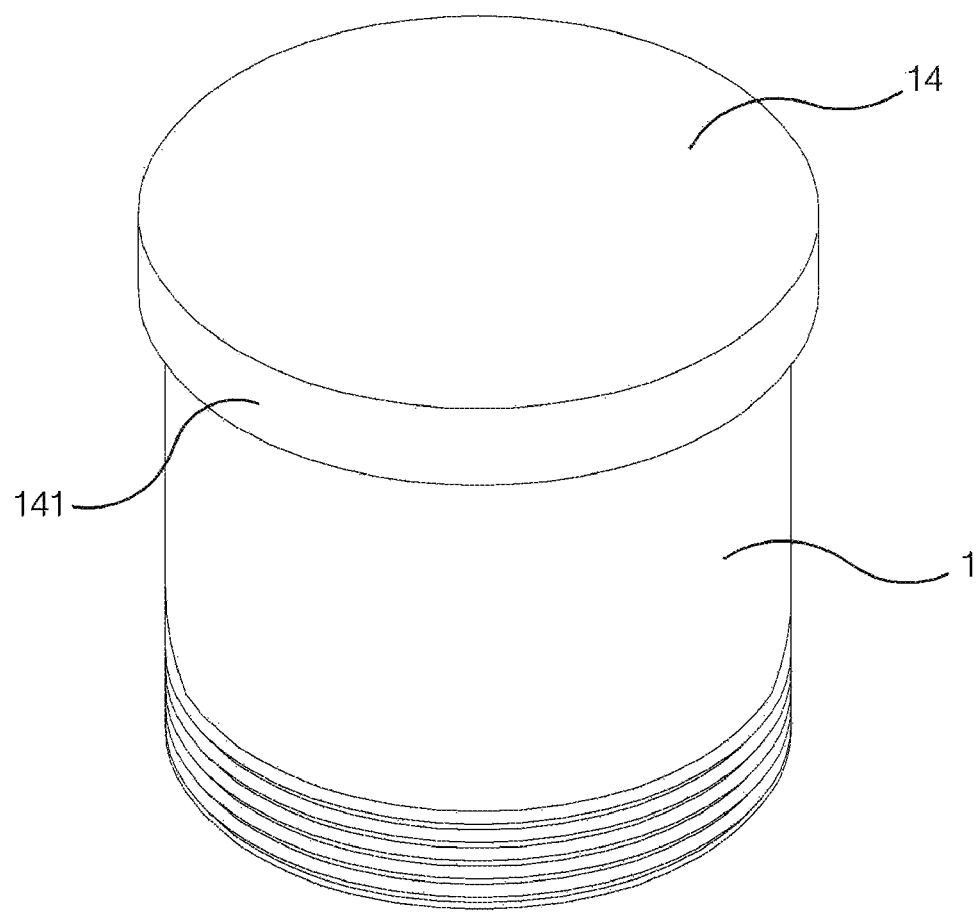
FIG. 1 is a perspective view illustrating an apparatus for Zgenerating functional water according to the present invention.

1: Container
11: Upper plate
12: Lower plate
13: Circumference protrusion plate
131: Upper engaging screw part
14: Separable opening and closing cover
141: Circumference plate 142: Engaging tap part
15: Lower engaging screw part
2: Water bottle connection part
21: First connection pipe
211: first tap part 212: Water passage plate 212a: Water passage hole
22: Second connection pipe
221: Size contracted pipe part 221a: Connection screw part
222: Size enlarged pipe part 222a: Second tap part
23: Connection packing pipe
231: Chamfering part
3: Lower opening and closing cover
41: Separable fixing unit
311: Lower tap part 312: Circumference plate 313: Engaging screw part
4: Functional water generating member
41: Alkali reducing agent
42: Charging part
421: Charging battery
43: Electric power supply jack
44: Substrate
45: Switch
46: Electrode
10: Water bottle
20: Opening part
30: Threaded part
40: Protruded protrusion

BEST MODES FOR CARRYING OUT THE INVENTION

The preferred embodiments of the present invention will be described with reference to the accompanying drawings. It is noted that the present invention may be implemented in different forms, and is not limited to the disclosure.

Figure 2:
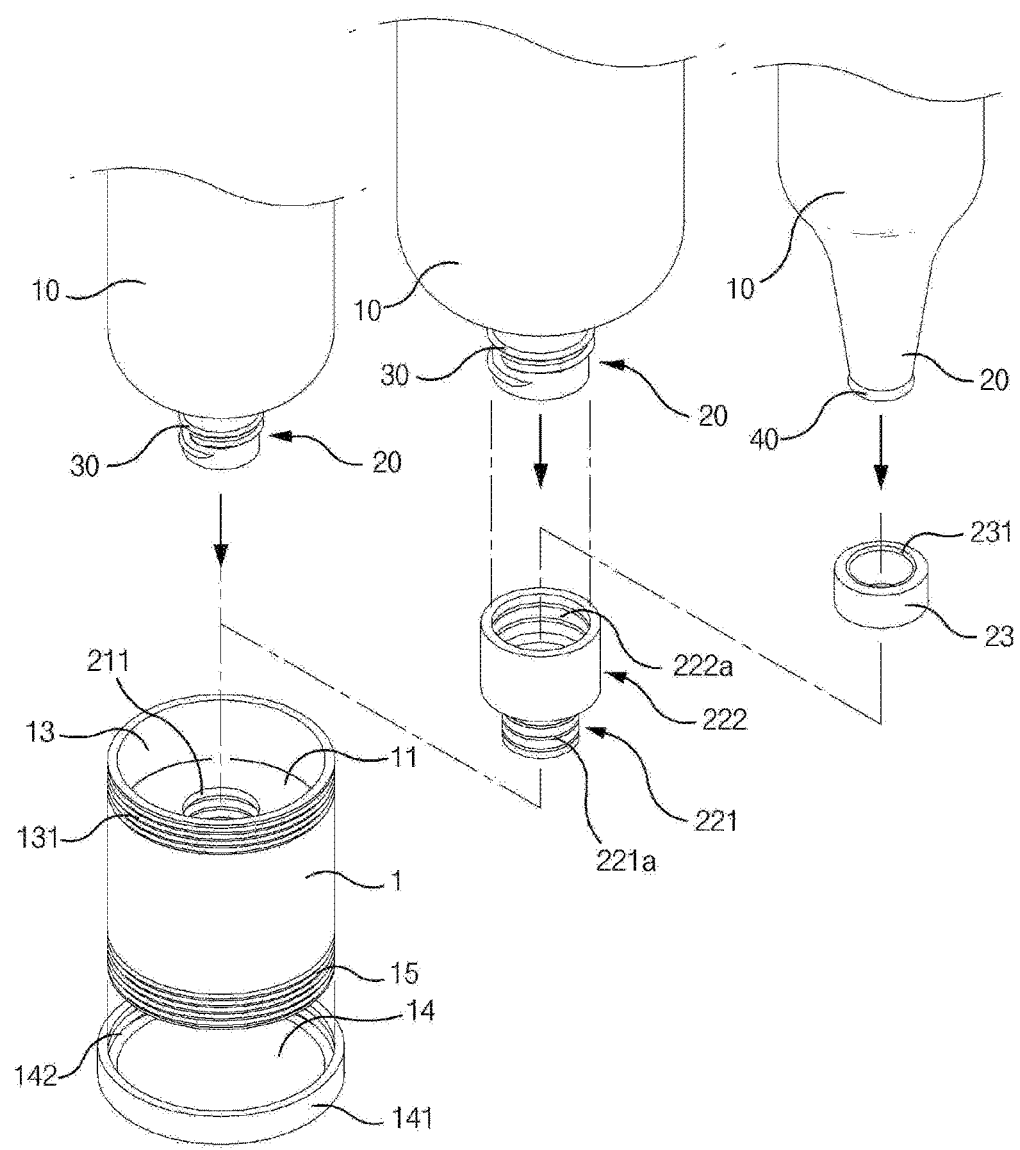
FIG. 2 is a disassembled perspective view illustrating an apparatus for generating functional water according to the present invention.
Figure 3:
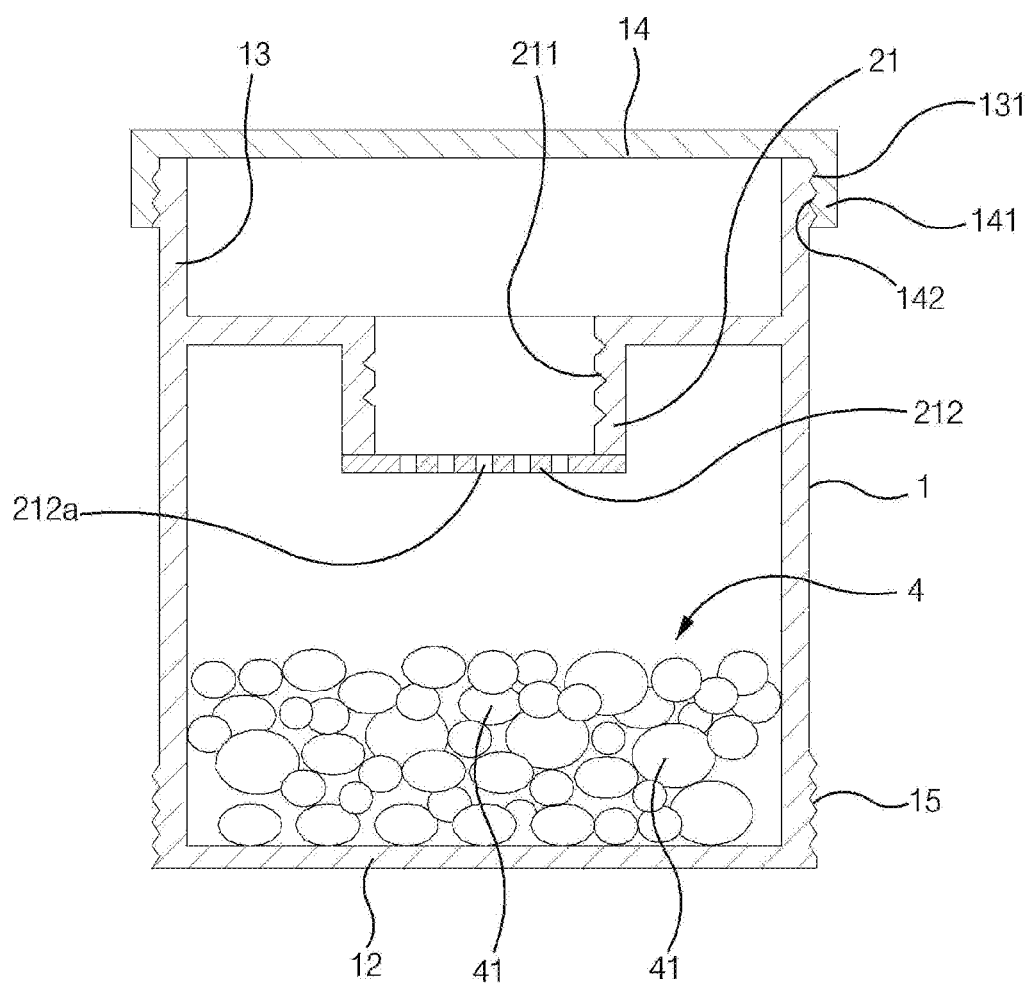
FIG. 3 is a cross sectional view taken along line A-A in FIG. 1.
Figure 4A:
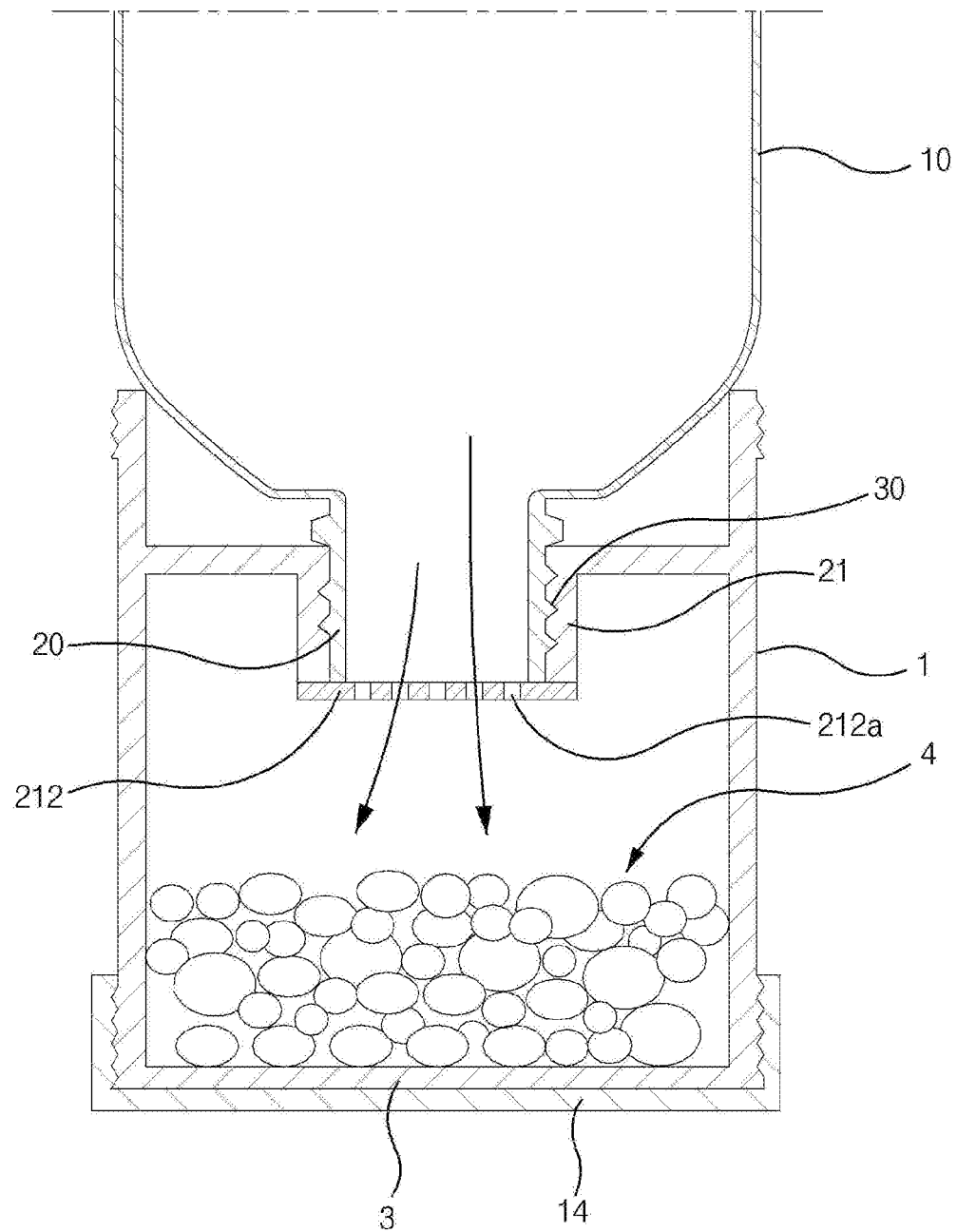
FIG. 4A is a view illustrating a state where a water bottle the outer diameter of an opening part of which is small is connected according to the present invention.
Figure 4B:
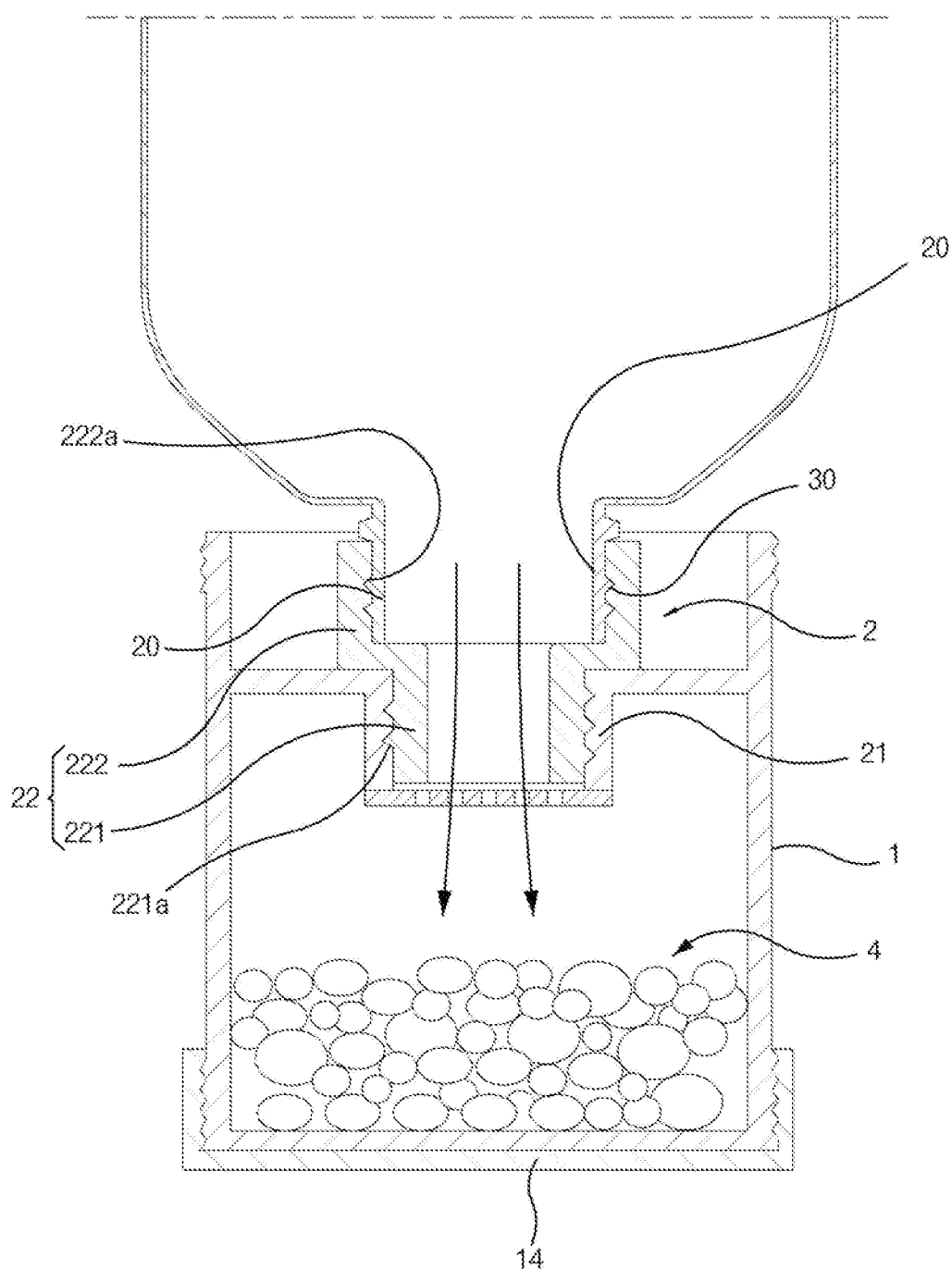
FIG. 4B is a view illustrating a state where a water bottle the outer diameter of an opening part of which is large is connected according to the present invention.
Figure 4C:
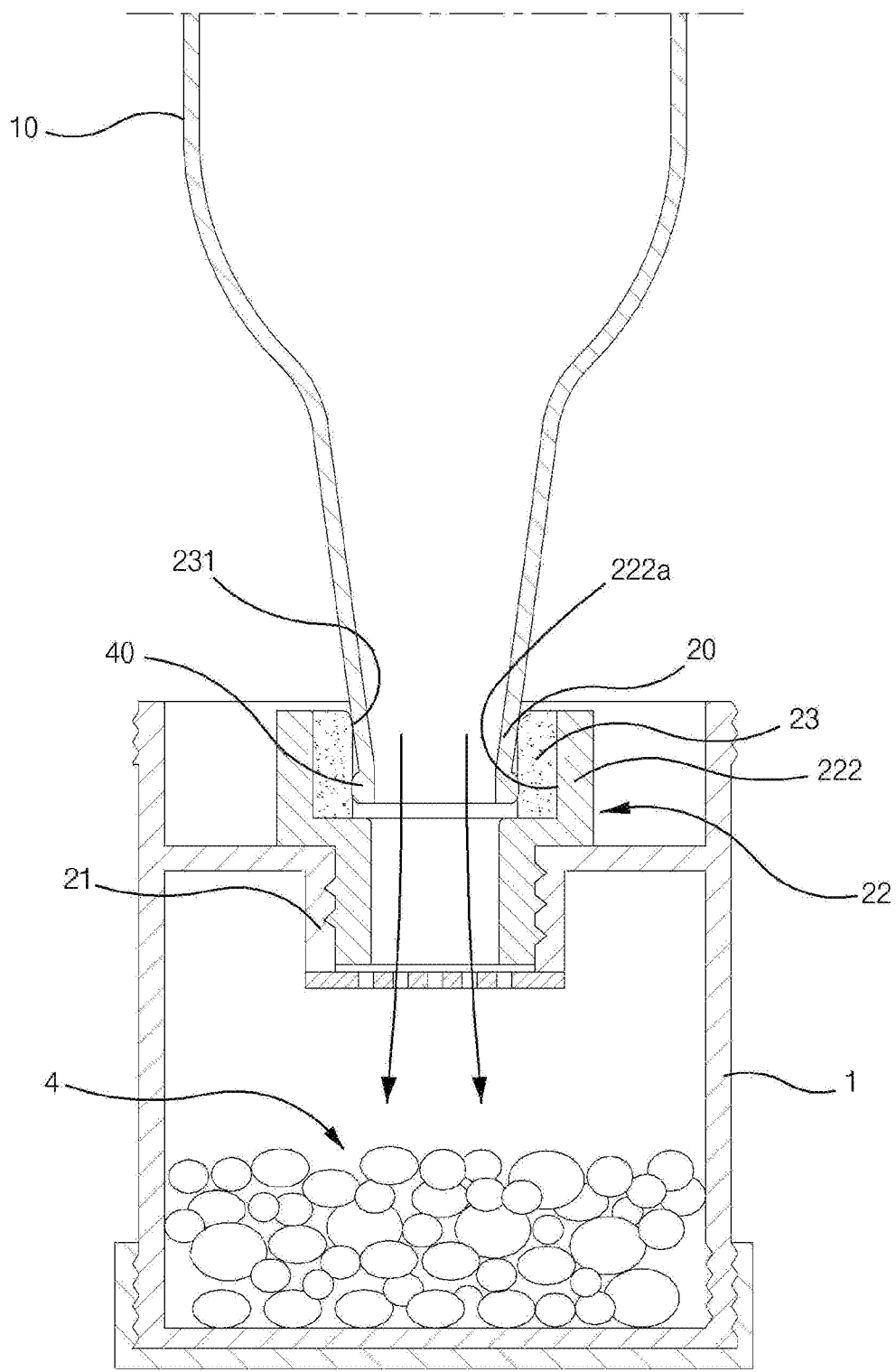
FIG. 4C is a view illustrating a state where a water bottle having protruded protrusions on its opening part is connected according to the present invention.

FIG. 1 is a perspective view illustrating an apparatus for generating functional water according to the present invention. FIG. 2 is a disassembled perspective view illustrating an apparatus for generating functional water according to the present invention. FIG. 3 is a cross sectional view taken along line A-A in FIG. 1. FIG. 4 is a view illustrating a use state of an apparatus for generating functional water according to the present invention. FIG. 4A is a view illustrating a state where a water bottle the outer diameter of an opening part of which is small is connected according to the present invention. FIG. 4B is a view illustrating a state where a water bottle the outer diameter of an opening part of which is large is connected according to the present invention. FIG. 4C is a view illustrating a state where a water bottle having protruded protrusions on its opening part is connected according to the present invention.

As illustrated in the drawings, the apparatus for generating functional water according to the present invention is connected, when in use, to an opening part 20 of a water bottle 10 the size of which is standardized and may include, but is not limited to, a container 1 which has a functional water generating member 4 in its inside and the upper and lower sides of which are blocked by an upper plate 11 and a lower plate 12, respectively; and a water bottle connection part 2 which is formed in the center of the upper plate 11 and is arranged communicating with the inside of the container 11, while allowing the opening part 20 of the water bottle 10 to be connected separable.

It is preferred that the container 1 is made visually transparent or semitransparent to see in the inside. The container 1 may be formed in a cylindrical shape or a polygonal cylindrical shape or a spherical shape. The drawings show that it is made in a cylindrical shape. It is preferred that the lower plate 12 is formed horizontal to allow the container 1 to easily stand on the floor. In addition, the upper plate 11 is configured to cover the upper side of the container 1. The functional water generating member 4 is provided in the inside of the container 1, and then preferably the upper plate 11 is fixedly attached to a circumference of the upper side of the container 1 in an ultrasonic wave method.

It is preferred that a circumference protrusion plate 13 protrudes upward from an upper side of a circumference of the upper plate 11 in order to prevent the water bottle 10 from standing inclined since the circumference of the upper side of the water bottle contacts close in a state where the water bottle stands upside down. Therefore, the present invention may allow to prevent the water bottle 10 from standing inclined by providing the circumference protrusion plate 13 in a state where the water bottle 10 stands upside down, whereupon it is possible to obtain stability during the conversion into functional water by moving the water bottle 10.

An upper engaging screw part 131 may be further formed on an outer circumferential surface of the circumference protrusion plate 13. A separable opening and closing cover 14 may be further provided at the upper engaging screw part 131 in order to cover separable the top of the container 1. In addition, the separable opening and closing cover 14 allows to prevent the inputs of any impurities, for example, dust, etc. into the water bottle connection part 2 and may include, but is not limited to, a circumference plate 141, wherein an engaging tap part 142 engaged separable to the upper engaging screw part 131 is formed on an inner circumferential surface of the circumference plate 141.

It is preferred that a lower engaging screw part 15 is further formed at a lower portion of an outer circumferential surface of the container 1 so as to engage for the separable opening and closing cover 14 to be stored, wherein an engaging tap part 142 formed at a circumference plate 141 of the separable opening and closing cover 14 is engaged to the lower engaging screw part 15. Therefore, according to the present invention, the lower engaging screw part 15 which may be engaged for the separable opening and closing cover 14 to be stored may be formed at a lower side of an outer circumferential surface of the container 1, whereupon it is possible to prevent any loss of the separable opening and closing cover 14 when drinking water after the water in the water bottle 10 is converted into functional water.

As illustrated in FIGS. 2 to 4, the water bottle connection part 2 according to the present invention is formed in the center of the upper plate 11 while communicating with the inside of the container 1, thus allowing the opening part 20 of the water bottle 10 to be connected separable.

It is preferred that the water bottle connection part 2, which has the above mentioned functions, may be formed of a first connection pipe 21 which stands vertical protruding downward in the center of the upper plate 11 and at an inner circumference a first tap part 211 is formed, wherein to the first tap part 211 a threaded part 30 is engaged, which is formed on an outer circumferential surface of the opening part 20 of the water bottle 10. In addition, the opening part 20 of the water bottle 10 is formed in a known tubular shape, and a threaded part 30 for engaging a closure of a water bottle is formed on an outer circumferential surface thereof.

In addition, the water bottle connection part 2 may further include a second connection pipe 22 which is engaged separable to the first tap part 211, as illustrated in FIGS. 2 and 4B, wherein the threaded part 30 formed on an outer circumferential surface of the opening part 20 of the water bottle 10 is engaged to the second connection pipe 22, so as to connect the water bottle 10 wherein the outer diameter of the standardized opening part 20 with the threaded part 30. In addition, it is preferred that the second connection pipe 22 may include, but is not limited to, a size contracted pipe part 221 which is formed at lower side and has on its outer circumferential surface a connection screw part 221a connected to the first tap part 211; and a size enlarged pipe part 222 which extends integral with an inner diameter increasing from the top of the size contracted pipe part 221, wherein on its inner circumferential surface, a second tap part 222a is formed, whose pitch circle is larger than a pitch circle of the first tap part 211.

In addition, the water bottle connection part 2 may further include, but is not limited to, a connection packing pipe 23 which is formed in a cylindrical shape as illustrated in FIGS. 2 and 4C to connect a water bottle 10 having a standardized opening part 20 with protruded protrusions 40 and fits into the inside of the second tap 222a of the second connection pipe 22, wherein a chamfering part 231 is formed at a circumference of the top of its inside, so a circumference protrusion 40 formed on an outer circumferential surface of the opening part 20 of the water bottle 10 is inserted in an interference fit way. The connection packing pipe 23 is made of a rubber material. In particular, the opening part 20 of the water bottle 10 is formed in a known tubular shape. A circumference protrusion 40 is formed on an outer circumferential surface so as to compress and engage a closure of the water bottle.

Therefore, the apparatus of the present invention may allow a container 1 to be connected with the aid of the first connection pipe 21 to a water bottle 10 wherein the outer diameter of the opening part 20 with a threaded part 30 is small and may allow the container 1 to be connected with the aid of the second connection pipe 22 to a water bottle 10 wherein the outer diameter of the opening part 20 with a threaded part 30 is large and may allow the container 1 to be connected to a water bottle 10 having an opening part 20 with a circumference protrusion 40. To this end, the present invention may allow a container to be connected to all kinds of the standardized water bottles 10 which are made of a synthetic resin material or a glass material and are available in the market.

As illustrated in FIG. 3, the functional water generation unit 4 according to the present invention may include an alkali reducing agent 41 which is provided in a grain type or a single solid form so as to reduce the water filled in the water bottle 10 into ionized water (reduced water). Since the above grain type or solid form alkali reducing agent 41 is known, so the detailed description thereon will be omitted.

Meanwhile, it is preferred that at a lower side of the first connection pipe 21, a water passage plate 212 with a plurality of water passage holes 212a are fixed so as to prevent the grain shaped alkali reducing agent 41 from inputting into the water bottle. In addition, it is most preferred that the water passage plate 212 may be fixedly attached to a lower side of the first connection pipe 21 by an ultrasonic wave method.

The operations of the apparatus for generating functional water according to the present invention will be described.

As illustrated in FIGS. 1 to 4, if the apparatus for generating functional water according to the present invention is actually used, the separable opening and closing cover 14 covering the top of the container 1 is removed. In addition, the first connection pipe 21 is connected to the opening part 20 positioning on the top of the water bottle 10 by inverting the container 1, thus connecting the container 1 to the top of the water bottle 10.

In a state where the water bottle 10 is turned upside down, and the apparatus for generating functional water is made to stand upright, the water bottle 10 and the container 1 are shaken or the water bottle 10 is made to stand and then is turned upside down, which procedure is repeatedly performed, whereupon the alkali reducing agent, which is the functional water generating member 4, filled in the inside of the container 1 comes to contact with the water of the water bottle 10 flowing into the container 1, so the water being filled into the container 1 is reduced into ionized water. Therefore, if the procedure wherein the water bottle 10 is shaken or is made to stand upright and then is turned upside down is repeatedly performed, the water filled in the water bottle 10 come in and goes out of the container 1, so the water filed in the water bottle 10 can be reduced into ionized water.

Next, in a state where the water bottle 10 is made to stand upright, the container 1 is separated from the water bottle 10, and then a user drinks the ionized water filled in the water bottle 10. In this way, the user can use the apparatus for generating functional water according to the present invention.

The present invention has advantages in the way that since the opening part 20 is standardized, the opening part 20 of the water bottle 10 which is available in the market can be directly connected to the container 1, so the water filled in the water bottle 10 can be reduced into ionized water, thus drinking it.

The present invention provides a structure which allows to connect the water bottle 10 which is available in the market, so it does not need to form any space to fill water, which allows easier carrying and minimized volume. Therefore, the apparatus for generating functional water according to the present invention is small in volume, which makes it possible to easily carry indoor or outdoor for the sake of an outdoor activity, for example, exercise or travel.

Figure 5:
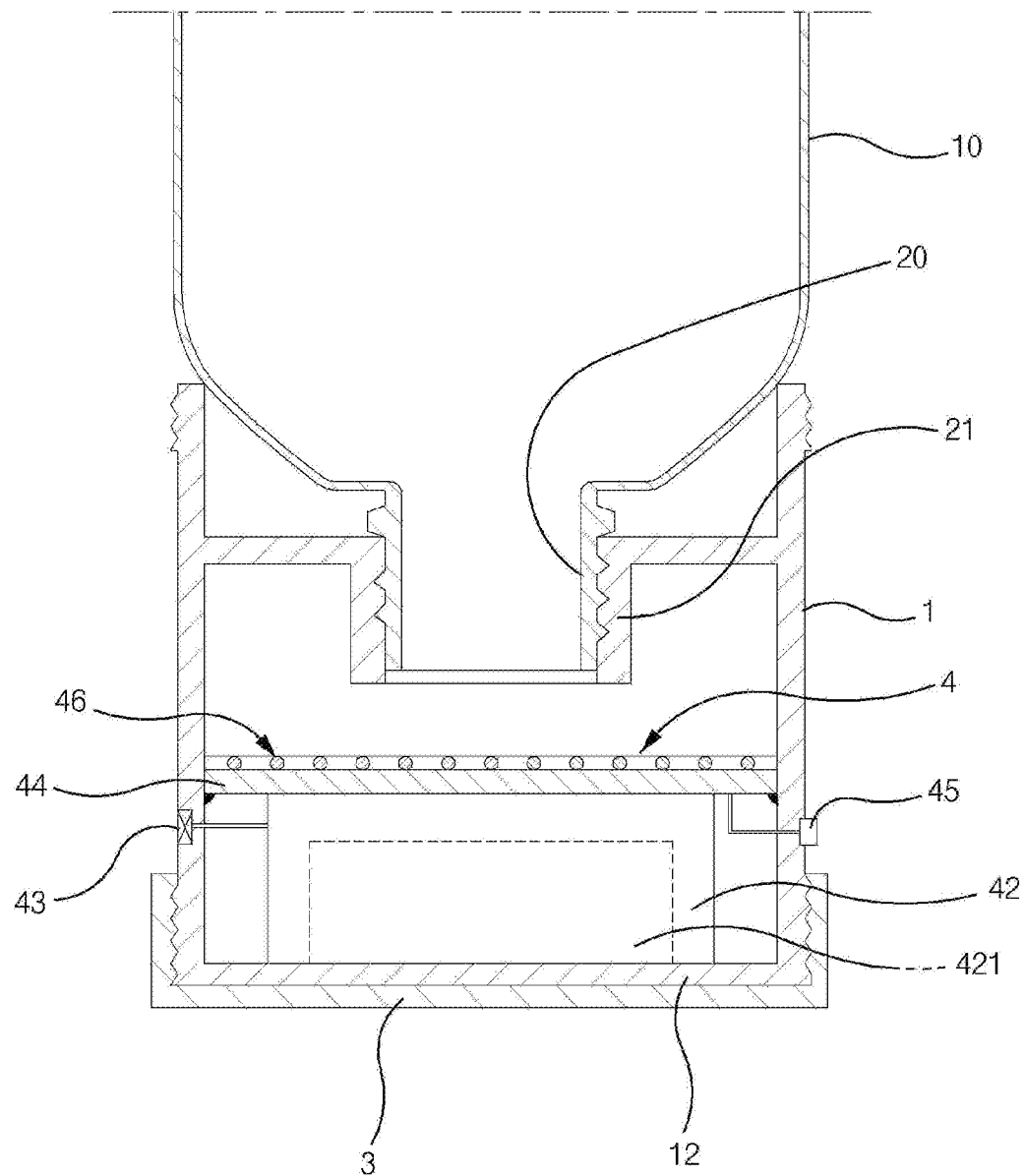
FIG. 5 is a cross sectional view illustrating an apparatus for generating functional water according to another embodiment of the present invention.

FIG. 5 is a cross sectional view illustrating an apparatus for generating functional water according to another embodiment of the present invention.

As illustrated in FIG. 5, the apparatus for generating functional water according to the another embodiment of the present invention has the same configuration except for the functional water generating member 4.

As illustrated in FIG. 5, it is preferred that in order to reduce the water in the water bottle into functional water, for example, oxygen water, sterilized and deodorized water or hydrogen water through electrolysis which uses electric power, the functional water generating member 4 forming the apparatus for generating functional water according to the another embodiment of the present invention may include, but is not limited to, a charging part 42 having a charging battery 421 fixed at the top of the lower plate of the container 1; an electric power supply jack 43 which is connected to the charging part 42 and extends to the circumference of the container 1; a substrate 44 which is fixedly arranged on the top of the charging part 4 and is connected with the charging unit 42; a switch 45 which is connected to the substrate 44 and extends toward the circumference of the container 1; and an electrode 46 which is fixedly arranged horizontal on the top of the substrate 44 and performs electrolysis with respect to water.

In addition, the electrode 46 allows to perform electrolysis with respect to water based on the supply of electric power and to reduce water into functional water, for example, oxygen water, sterilized and deodorized water or hydrogen water. In addition, the above electrode 46 in general is coated with platinum, titanium etc. The substrate configured to supply electric power to the electrodes is one known in the conventional technology, so the detailed descriptions thereon will be omitted. It is preferred that the surfaces of the charging part 42 and the substrate 44 are processed for waterproof so as to prevent the inputs of water.

In case where the apparatus for generating functional water according to another embodiment of the present invention is actually used, the water bottle is connected to the container, and the water bottle 10 is turned upside down, and the functional water generating apparatus is made to stand upright. In this state, electric power is supplied to the electrodes 46 by operating the switch 45 at a circumference of the container 1, and electrolysis is performed with respect to the water through the electrodes 46, and the water in the water bottle 10 flowing into the container 1 is reduced into oxygen water or sterilized and deodorized water or hydrogen water. To this end, if a procedure wherein the water bottle 10 is made to stand upright or is turned upside down, with electric power supplied to the electrodes, is repeatedly performed, the water filled in the water bottle 10 comes in and goes out of the container 1, whereupon the water filled in the water bottle 10 can be reduced into functional water, for example, oxygen water, sterilized or deodorized water or hydrogen water.

Next, with the water bottle 10 standing upright, the container 1 is separated from the water bottle 10, so the user can drink functional water filled in the water bottle 10. Consequently, the user can use the apparatus for generating functional water according to another embodiment of the present invention.

As the present invention may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

The invention claimed is:

1. An apparatus for generating functional water, comprising:
    a container which is configured to accommodate a functional water generating means, wherein upper and lower sides of the container are blocked by an upper plate and a lower plate;
    a water bottle connection part which is formed in the center of the upper plate while communicating with the inside of the container, wherein the water bottle connection part separably connects to an opening part of a water bottle, the water bottle connection part comprising a first connection pipe which stands vertical protruding downward in the center of the upper plate and comprises a first tap part formed at an inner circumference of the first connection pipe, wherein a threaded part formed on an outer circumferential surface of an opening part of a water bottle is engageable to the first tap part; and
    a second connection pipe which is separably engaged to the first tap part, wherein a threaded part formed on an outer circumferential surface of an opening part of a water bottle is engageable to the second connection pipe, the second connection pipe comprises a narrower pipe part which is formed at a lower portion thereof and has a connection screw part formed at an outer circumferential surface thereof and engages the first tap part; and a wider pipe part integrally extends from the top of the narrower pipe part and having a larger inner diameter than the narrower pipe part, wherein on an inner circumferential surface of the wider pipe part, a second tap part is formed, the pitch circle of the second tap part is larger than the pitch circle of the first tap part.

2. The apparatus of claim 1, wherein the water bottle connection part further includes:
    a rubber connection packing pipe which is formed in a cylindrical shape and fits into the inside of the second tap part of the second connection pipe, wherein a chamfering part is formed at a circumference of the top of the inside, and a circumference protrusion formed on an outer circumferential surface of a opening of a water bottle is inserted in an interference fit.

3. The apparatus of claim 1, wherein the functional water generating means is formed of an alkali reducing agent provided in as grains or as a single solid form, and a water passage plate with a plurality of water passage holes is further fixed at a lower side of the first connection pipe.

4. The apparatus of claim 1, wherein the container further includes:
    a separable opening and closing cover configured to cover the top of the container, wherein there are provided a circumference protruding plate which is formed protruding upward from an upper side of a circumference of the upper plate; an upper engaging screw part formed on an outer circumferential surface of the circumference protruding plate; and an engaging tap part which is formed on an inner circumferential surface of the circumference plate and is separably engageable to the upper engaging screw part.

5. The apparatus of claim 4, wherein the container further includes:
    a lower engaging screw part which is formed on a lower side of an outer circumferential surface of the container, wherein an engaging tap part formed on a circumference plate of the separable opening and closing cover is engageable to the lower engaging screw part.

6. The apparatus of claim 1, wherein the functional water generating means includes:
    a charging part having a charging battery fixed at the top of the lower plate of the container;
    an electric power supply jack which is connected to the charging part and extends to a circumference of the container;

a substrate which is fixedly arranged on the top of the charging part and is connected with the charging unit;
a switch which is connected to the substrate and extends toward a circumference of the container; and
an electrode which is fixedly arranged horizontal on the top of the substrate and performs electrolysis with respect to water.

\* \* \* \* \*